United States Patent
Khedkar et al.

(10) Patent No.: US 7,176,001 B1
(45) Date of Patent: Feb. 13, 2007

(54) MANUFACTURE AND PURIFICATION OF CYCLOSPORIN A

(75) Inventors: Anand Prakash Khedkar, Karnataka (IN); Pampapathy Subramaniyam, Karnataka (IN); Konayakanahalli Nanjunda Swamy Anand, Karnataka (IN); Melarkode Ramkrishna, Karnataka (IN); Shreehas Pradeep Tambe, Karnataka (IN); Sambasivam Ganesh, Karnataka (IN); Anindya Sircar, Karnataka (IN); Shrikumar Suryanarayan, Karnataka (IN)

(73) Assignee: Biocon Limited, Bangalore (IN)

( * ) Notice: Subject to any disclaimer, the term of this patent is extended or adjusted under 35 U.S.C. 154(b) by 0 days.

(21) Appl. No.: 10/220,226

(22) PCT Filed: Feb. 29, 2000

(86) PCT No.: PCT/IN00/00018

§ 371 (c)(1),
(2), (4) Date: Oct. 23, 2003

(87) PCT Pub. No.: WO01/64935

PCT Pub. Date: Sep. 7, 2001

(51) Int. Cl.
*C12P 21/04* (2006.01)

(52) U.S. Cl. ..................... 435/71.1; 435/71.3; 435/243

(58) Field of Classification Search .................. 435/47, 435/71.1, 71.3, 243
See application file for complete search history.

(56) References Cited

U.S. PATENT DOCUMENTS

| | | | | |
|---|---|---|---|---|
| 3,904,476 | A * | 9/1975 | Leavitt | 435/248 |
| 4,117,118 | A | 9/1978 | Härri et al. | 435/71.1 |
| 4,288,431 | A * | 9/1981 | Traber et al. | 514/11 |
| 4,466,885 | A * | 8/1984 | Ronden | 208/188 |
| 4,569,793 | A * | 2/1986 | Dong et al. | 544/370 |
| 4,762,923 | A * | 8/1988 | Lam et al. | 540/455 |
| 4,843,054 | A * | 6/1989 | Harper | 502/175 |
| 5,256,547 | A * | 10/1993 | Rudat et al. | 435/71.1 |
| 5,409,816 | A * | 4/1995 | Lundell et al. | 435/71.3 |
| 6,383,532 | B1 * | 5/2002 | Lim et al. | 426/52 |
| 6,664,095 | B1 * | 12/2003 | Suryanarayan et al. | 435/243 |

FOREIGN PATENT DOCUMENTS

| | | |
|---|---|---|
| CA | 2108655 | 4/1995 |
| EP | 0725076 A1 | 8/1996 |
| GB | 2227489 A | 8/1990 |
| WO | WO 96/12032 | 4/1996 |
| WO | WO 97/46575 | 12/1997 |
| WO | WO 00/29544 | 5/2000 |

OTHER PUBLICATIONS

M.V. Ramana Murthy, E.V.S. Mohan, A.K. Sadhukhan, "Cyclosporin-A production by Tolypocladium inflatum using solid state fermentation" Process Biochemistry, Oxford (1999) 34(3), pp. 269-280.*

Maria Jesus Cantalejo, Jose Maria Carresco, Enrique Hernandez, "Incidence and Distribution of *Fusarium* species associated with feeds and seeds rom Spain", Rev. Iberoam Micol. 1998; 15,pp. 36-39.*

David Cummings, "Dealing with turbid water", Department of Primary Industries, Jan. 1997, www.dpi.vic.gov.au/dpi/nreninf.nsf, pp. 1-4.*

Borel, Jean F. (Editor) *Progress in Allergy, vol. 38: Ciclosporin.* Karger, Basel, Switzerland. 1986 (bibliographic information only).

Murthy, M.V. Ramana et al. "Cyclosporin A production by Tolypocladium inflatum using solid-state fermentation." Process Biochemistry, Oxford (1999). 34(3), pp. 269-280 (abstract only).

Sekar, C. et al. "Effect of precursur amino acids on the production of cyclosporin a by solid state fermentation." Indian Journal of Microbiology, vol. 36, Dec. 1996. pp. 231-232.

Sekar, C. et al. "Production of Cyclosporin A by solid state fermentation." Bioprocess Engineering, vol. 17, 1997. pp. 257-259.

* cited by examiner

*Primary Examiner*—Jean C. Witz
*Assistant Examiner*—Laura Schuberg
(74) *Attorney, Agent, or Firm*—Sidley Austin LLP

(57) ABSTRACT

The present invention provides an improved method for the manufacture of Cyclosporin A is disclosed. Cyclosporin A is produced by solid state fermentation of *Fusarium solani* in a bioreactor under optimal fermentation parameters. The product is extracted and further purified by treating with alum and subsequent chromatographic procedures to get pharmaceutical acceptable purity.

12 Claims, No Drawings

MANUFACTURE AND PURIFICATION OF CYCLOSPORIN A

FIELD OF THE INVENTION

The present invention relates to an improved method for the manufacture and purification of Cyclosporin A (CsA).

BACKGROUND

CsA is a member of a group of cyclic undecapeptides with anti-inflammatory, immunosuppressive, antifungal and antiparasitic properties. The immunomodulatory properties are of particular interest in medicine, since they are important in prevention of organ rejection in transplantation surgery and for autoimmune diseases.

Cyclosporins are a class of compounds which were first described in Swiss patents 589716 and 603790. They have been reviewed in the monograph by Borel [Cyclosporin, Progress in Allergy (1986) 38, Karger Press] discussing the chemical structure and the biological-pharmacological properties.

Over 20 different cyclosporins are produced by fungi all having varying amino acid composition. CsA is the major component and currently enjoys the most widespread clinical use.

In extensive screening experiments, numerous fungal species were found to have CsA forming properties. Dreyfuss [Sydowia (1986) 39, 22–36] described an exclusively Cyclosporin forming ability for *Cylindrocarpon* and *Fusarium*. Cyclosporin formation is also reported from following—*Tolypocladium geodes, Trichoderma virile, Neocosmospora vasunfecta, Isaria* spp., *Verticillium* spp., *Acremonium* spp. and *Beauveria nivea*.

*Sesquicilliopsis rosariensis* F 605 with 3150 mg/L after 14 days of submerged fermentation and *Tolypocladium inflatum* Wb 6-5 with 1100 mg/L after 11 days of fermentation are known to be high producers (U.S. Pat. No. 5,256,547, 1993). *Tolypocladium inflatum* KD 461, a mutant when supplemented with L-leucine and L-valine produced 8920 mg/L after 13 days (WO Patent No. 96/12032, 1996).

*Tolypocladium inflatum* strains have been used in solid state fermentation for Cyclosporin fermentations. Strains producing 1.95 g/kg to 4.84 g/kg of wheat bran during 5–10 days of fermentation have been reported [Balaraman and Mathew EP No. 0 725 076 (1996); Sekar and Balaraman, Ind. J. Microbiol. (1996) 36, 231–234; Sekar et al, Bioprocess Engg. (1997) 18, 257–259; Murthy et al, Process Biochem. (1999) 34, 269–280].

The economics of using a producing strain, the described volume-time-yields in the above process are not satisfactory. Further, there are difficulties of maintaining a low temperature of 25° C. There are also disadvantages in isolation and purification of different cyclosporins in this process.

The patent specification EP 0 725 076, also discloses a process for the manufacture of CsA by solid state fermentation—but uses a *Tolypocadium* sp. and an uncontained system. Since the fermentation process disclosed in EP 0725 076 is not contained it doesn't assure full safety for the cytotoxic fermentation products like CsA—making the process industrially unattractive.

The purification processes to isolate pharmacopoeial grade CsA used conventionally are extraction of fermented biomass using an organic solvent, evaporation of solvent, reextraction of residue, concentration and then subjecting the residue to various chromatographic processes to separate CsA from other cyclosporins and impurities viz., gel filtration typically LH-20 (U.S. Pat. Nos. 4,117,118 and 5,256, 547) and/or silica gel or alumina columns (U.S. Pat. No. 4,117,118) or adsorption resin columns (patent No. WO 97/46575). Final yields obtained from the conventional processes are typically in the range of 40% to 60%. Removal of the lipids from the fermented media is done by using pet ether, hexane, acetone, methanol or a mixture of these (British patent No.GB 2,227,489). CsA being mixable in these lipids as well as in the mixture of acetone and petroleum ether, a significant amount of CsA is lost during this step.

Super critical fluid extraction has also been reported to have been used for separation of cyclosporin using super critical carbon dioxide (Canadian patent No. CA 2,108,655). This process has economic limitations for its commercial application.

DESCRIPTION OF THE INVENTION

The objects of this invention therefore are:
to provide a novel bioreactor for a contained solid state fermentation such that the fermenting micro-organism and the fermentation products it produces are kept isolated from the outside environment during the course of fermentation
to reduce solvent consumption required in large quantities for extracting CsA from fermentation broth or the aqueous residue
to produce higher yield and purity of CsA
to assure full safety for the cytotoxic fermentation products like CsA.
to reduce the period for fermentation and to control the temperature easily.

To achieve the said objectives this invention provides an improved method for the manufacture and purification of cyclosporin A comprising:
loading a contained bioreactor with solid state nutritive matrix and sterilizing it,
mixing the said sterilized solid state nutritive matrix with *Fusarium* sp.,
incubating the said inoculated solid state nutritive matrix for 4–6 days at 25–30° C.,
extracting the fermented matrix with an organic solvent,
- concentrating the organic solvent extract and treating with 0.1 to 5.0% alum for 2 to 6 hours to obtain CsA precipitate, followed by filtration using a filter aid,
- dissolving the said filter aid cake in a hydrocarbon organic solvent and concentrating to get a residue,
- subjecting the said residue dissolved in an alcohol to gel filtration,
- pooling the CsA containing fractions and subjecting to silica gel chromatography, and removing the organic solvent by distillation,
- dissolving the solid obtained in 2 to 6 times the volume of an organic solvent and allowing it to chill at −10 to −45° C. for 2 to 8 hours.
- filtering the organic solvent to get pure cyclosporin.

The said *Fusarium* sp. is *Fusarium solani*, which is in the form of a macroconidial suspension.

The said contained bioreactor allows solid state fermentation to be carried out in a manner such that the fermentation micro-organisms and the fermentation products produced are kept isolated from the outside environment during the course of fermentation. The said contained bioreactor is "PLAFRACTOR".

The solid state nutritive matrix is selected from wheat bran, rice bran, soya grits or rice grits.

The organic solvent used for extraction is selected from acetone, methanol, toluene, benzene or ethyl acetate.

The alum used for treating the aqueous concentrate is either potash alum or ammonium alum.

The filter aid is selected from celite, perlite or alumina

The solvent used to dissolve the residue is selected from cyclohexane, toluene, benzene.

The gel filtration matrix is Sephadex LH-20.

The alcohol used as an eluant for gel filtration is selected from methanol, ethanol or iso-propanol.

The mobile phase used is acetone, hexane or a mixture of these.

The residue obtained is dissolved in 2 times the volume of acetone and chilling at −20° C.

The novel contained bioreactor is 'PLAFRACTOR' and is capable of sterilizing the solid state fermentation media, cooling it to the required temperature, fermenting at the desired set conditions, in situ extraction of the is end product, recovery of the solvents and post harvest sterilization (International publication no. WO 00/29544). The 'PLAFRACTOR', a novel bioreactor for solid state fermentation is a unique invention of Biocon India Limited The modular construction of this bioreactor provides multiple modules stacked on top of one another, each with a base connected to frame for holding the solid medium in isolation from the exterior environment. The construction of the bioreactor allows solid state fermentation to be carried out in a manner such that the fermenting microorganisms and the fermentation products it produces are kept isolated from the outside environment during the course of the fermentation. This containment of the fermentation process is of significant importance when working with microbial metabolites, which are cytotoxic in nature e.g. Cyclosporin. An important aspect of the bioreactor is a mechanism of heat removal resulting in stringent temperature control of the fermentation process. In comparison, maintaining a constant temperature of growth in solid state fermentation using tray cultures is not efficient. The base plate of the bioreactor has multiple channels called noncommunicating channels that carry heating and cooling fluids sandwiched between two sheets. Heat is transferred to and from the modules by conduction. In this way the temperature of the module is precisely maintained to meet the specific requirement of different microorganisms.

The base of the module contains a second set of channels, the communicating channels to deliver sterile air as supply of oxygen into the solid substrate bed for optimum growth of organism. Moisture loss because of passage of sterile air is significantly reduced by regularly reversing the direction of airflow every few hours. Using this, homogeneity in moisture content is maintained throughout the bioreactor. These aspects provide ample convenience over previous SSF methodologies that require multiple manipulations at each step of the fermentation process.

The invention will now be described with reference to the following examples:

EXAMPLE 1

Heavily sporulated slants of *Fusarium solani* was taken and 5 mL of sterile distilled water was added to it. It was shaken thoroughly and 500 L of the spore suspension was spread on MEA (Malt Extract Agar) plates and incubated at 30° C. for 7 days. After 7 days the macroconida lodged as a slime is scraped by a sterile loop in sterile distilled water. This macro conidial suspension, devoid of mycelial bits is used as the inoculum. 15 Kg of wheat bran was loaded on the contained bioreactor of approximately 22600 $cm^2$ of plate area. The bioreactor was sterilized by sending steam simultaneously into the communicating and the noncommunicating channels to heat the bioreactor and its contents to a temperature of 121° C. for 1–2 hours. The steam pressure was released and simultaneously sterile air was sent into the communicating channels while cooling water at approximately 30° C. was sent into the noncommunicating channels.

The master seed for inoculation of culture was a 104 macroconidia/ml suspension of *Fusarium solani* in 14 L of sterilized dist. water. This was used to inoculate the sterilized wheat bran so that the final moisture after inoculation was 65%. The inoculum was mixed thoroughly with the sterilized bran. Sterile airflow at a rate of 20 Lpm on the first day, 40 Lpm on second and third day and 20 Lpm on fourth and fifth day was sent into the bioreactor continuously. The temperature was controlled at 30° C. for all 5 days by conductive heating and cooling. The CsA production titres was assayed following extraction using the HPLC.

EXAMPLE 2

The contained bioreactor was sterilized and inoculated as in Example 1. In this experiment, the temperature was maintained at 25° C. for all 5 days. The CsA production titres was assayed following extraction using the HPLC.

EXAMPLE 3

The contained bioreactor was sterilized and inoculated as in Example 1. In this experiment, rice bran was used instead of wheat bran and the temperature was maintained at 30° C. for all 5 days. The CsA production titres was assayed following extraction using the HPLC.

EXAMPLE 4

5 Kg. fermented wheat bran obtained from Example 2 was then extracted by using methanol. 10 L of methanolic extract was collected, analyzed and taken for further processing. The extraction efficiency of methanol was found to be 98%, as quantitated by HPLC.

EXAMPLE 5

The extract obtained from Example 4 was concentrated by azeotropic distillation to remove methanol, leaving behind 1.5 lts of aqueous residue. To this aqueous residue, 2.5% (w/v) potassium alum was added and allowed to stand for 3 hrs. After 3 hrs. precipitate of cyclosporin was found floating at the surface of the liquid. This precipitate was separated by filtration through a CELITE (diatomaceous earth) bed. Recovery of cyclosporin by this precipitation was found to be 100%. Precipitate trapped on the CELITE (diatomaceous earth) bed was redissolved completely in 400 ml of cyclohexane. Cyclohexane was removed by distillation to leave behind 17.55 gm of solid residue containing 10.5 gm of CsA. This residue dissolved in methanol was subjected to first gel filtration using Sephadex LH-20 with methanol as an eluent. The fractions containing CsA were pooled and further subjected to silica gel (230–400 mesh) column chromatography, with acetone and hexane mixture (3:7) as the mobile phase. Fractions containing only CsA were pooled together and solid CsA was obtained by removing the solvents completely by vacuum distillation. Desired quality of CsA crystals were obtained by dissolving the solid CsA powder obtained from chromatography in 3 times the volume of acetone and chilling at −20° C. Crystals obtained after filtration were found to be of acceptable pharmaceutical grade purity as assayed by HPLC.

EXAMPLE 6

The extract obtained was processed as in Example 4. In this experiment Bioreactor was sterilized and inoculated as in Example 2. In this experiment, 1.0% (w/v) of ammonium alum was used instead of potash alum. Crystals obtained after acetone crystallization were found to be of acceptable pharmaceutical grade purity as assayed by HPLC.

The examples given above are not exhaustive.

The present invention has the following advantages over the other reported methods
  (i) Fermentation in a bioreactor, which is fully contained as a result assuring full safety for the cytotoxic fermentation products like CsA.
  (ii) Less fermentation time and easier control of temperature making the process economically attractive.
  (iii) Fewer steps for the isolation and purification to get the pure product, thus saving processing time and additional expenses.
  (iv) High efficiency of the alum treatment step during the purification process results in higher yields.

The invention claimed is:

1. A method for the manufacture and purification of cyclosporin A (CsA) comprising:
  loading a contained bioreactor with solid state nutritive matrix and sterilizing it, wherein the bioreactor comprises multiple stacked modules, each with a base connected to a frame, and wherein each base contains a plurality of communicating and noncommunicating channels,
  mixing the said sterilized solid state nutritive matrix with *Fusarium* sp. used as inoculum,
  incubating the said inoculated solid state nutritive matrix for 4–6 days at 25–30° C.,
  extracting the fermented matrix with an organic solvent,
  concentrating the organic solvent extract and treating with 0.1 to 5.0% alum for 2 to 6 hours to obtain a CsA precipitate, followed by filtration using a filter aid, dissolving the CsA precipitate in a hydrocarbon organic solvent and concentrating to get a residue,
  treating the residue with alcohol and subjecting the residue to gel filtration to produce CsA containing fractions,
  pooling the CsA containing fractions and subjecting to silica gel chromatography, elution and removing the organic solvent by distillation to produce a concentrate, dissolving the concentrate obtained in 2 to 6 times the volume of an organic solvent and allowing to chill at −10 to −45° C. to 2 to 8 hours, and
  filtering the organic solvent to get pure cyclosporin A.

2. The method as claimed in claim 1 wherein the *Fusarium* sp. used as inoculum is *Fusarium solani*.

3. The method as claimed in claim 2 wherein the *Fusarium solani* used as inoculum is in the form of a macroconidial suspension.

4. The method as claimed in claim 1 wherein the said contained bioreactor allows solid state fermentation to be carried out in a manner such that the fermentation microorganisms and the fermentation products produced are kept isolated from the outside environment during the course of fermentation.

5. The method as claimed in claim 1 wherein the solid state nutritive matrix is wheat bran, rice bran, soya grits or rice grits.

6. The method as claimed in claim 1 wherein the organic solvent used for extraction is acetone, methanol, toluene, benzene or ethyl acetate.

7. The method as claimed in claim 1 wherein the alum used for treating the aqueous concentrate is either potash alum or ammonium alum.

8. The method as claimed in claim 1 wherein the filter aid is (diatomaceous earth), perlite or alumina.

9. The method as claimed in claim 1 wherein the solvent used to dissolve the concentrate is cyclohexane, toluene or benzene.

10. The method as claimed in claim 1 wherein the alcohol used as an eluant for gel filtration is methanol, ethanol or iso-propanol.

11. The method as claimed in claim 1 wherein an eluent is used for the silica gel chromatography is acetone, hexane or a mixture thereof.

12. The method as claimed in claim 1 wherein the concentrate is dissolved in 2 times the volume of acetone and chilled at −20° C.

* * * * *